(12) United States Patent
Masumoto et al.

(10) Patent No.: US 7,612,227 B2
(45) Date of Patent: Nov. 3, 2009

(54) PROCESSES FOR PRODUCING 3-METHYL-2-BUTENYL ACETATE

(75) Inventors: Katsuhisa Masumoto, Ibaraki (JP); Makoto Itagaki, Katano (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/590,991

(22) PCT Filed: Mar. 22, 2005

(86) PCT No.: PCT/JP2005/005656

§ 371 (c)(1),
(2), (4) Date: Jul. 16, 2008

(87) PCT Pub. No.: WO2005/092828

PCT Pub. Date: Oct. 6, 2005

(65) Prior Publication Data

US 2008/0275268 A1    Nov. 6, 2008

(30) Foreign Application Priority Data

Mar. 25, 2004 (JP) ............................. 2004-088617
Jul. 2, 2004 (JP) ............................. 2004-196477

(51) Int. Cl.
*C07C 67/02* (2006.01)

(52) U.S. Cl. ...................... 560/249; 560/261

(58) Field of Classification Search ...................... None
See application file for complete search history.

(56) References Cited

U.S. PATENT DOCUMENTS

| | | |
|---|---|---|
| 3,959,278 A | 5/1976 | Wood et al. |
| 4,734,239 A | 3/1988 | Diamantoglou et al. |
| 5,488,141 A | 1/1996 | Bauer, Jr. et al. |
| 5,872,277 A | 2/1999 | Babler |
| 6,034,268 A | 3/2000 | Surburg et al. |
| 6,278,016 B1 | 8/2001 | Babler |

FOREIGN PATENT DOCUMENTS

JP        5-140035 A       6/1993

OTHER PUBLICATIONS

N. Ostergaard et al., "Scope and Limitations of chiral bis(oxazoline) ligands in the copper-catalysed asymmetric cyclopropanation of trisubstituted alkenes", Tetrahedron 57, (2001), pp. 6083-6088.
J. Ward et al., "Synthesis of (2E)-4-hydroxy-3-methylbut-2-enyl diphosphate, a key intermediate in the biosynthesis of isoprenoids", J. Chem. Soc., Perkin Trans. 1, (2002), pp. 710-712.
N. Kann et al., "New Functionalized Horner-Wadsworth-Emmons Reagents: Useful Building Blocks in the Synthesis of Polyunsaturated Aldehydes. A Short Synthesis of (±)-(E,E)-Coriolic Acid", J. Org. Chem. 55, (1990), pp. 5312-5323.
A. Chakraborti et al., "Electrostatic catalysis by ionic aggregates: scope and limitations of $Mg(ClO_4)_2$ as acylation catalyst", Tetrahedron 59, (2003), pp. 7661-7668.
A. Charaborti et al., "Indium (III) chloride as a new, highly efficient, and versatile catalyst for acylation of phenols, thiols, alcohols, and amines", Tetrahedron Letters 44, (2003), pp. 6749-6753.
"The Chemical Society of Japan, Dai 4 pan Jikken Kagaku Koza 22, Yuki Gosei IV—San • Amino San • Peptide-, Maruzen Co., Ltd., (1992), 50-51".
I. Hogan et al., "An Efficient Synthesis of Streptindole", Synthesis, (1984), pp. 872.

*Primary Examiner*—Paul A Zucker
(74) *Attorney, Agent, or Firm*—Sughrue Mion, PLLC

(57) ABSTRACT

The present invention relates to a method for producing 3-methyl-2-butenyl acetate which comprises reacting 3-methyl-2-buten-1-ol with acetic anhydride in the presence of an inorganic base catalyst and a method for producing purified 3-methyl-2-butenyl acetate which comprises subjecting crude 3-methyl-2-butenyl acetate to a step (A) of contacting it with an aqueous solution of an alkali metal hydrogen sulfite, or a step (B) of contacting it with an aqueous solution of a base, or both steps (A) and (B).

5 Claims, No Drawings

PROCESSES FOR PRODUCING 3-METHYL-2-BUTENYL ACETATE

TECHNICAL FIELD

The present invention relates to a method for producing 3-methyl-2-butenyl acetate.

BACKGROUND ART 3-methyl-2-butenyl acetate is a useful compound as a raw material of various chemicals such as pharmaceuticals and agricultural chemicals. For example, 3-methyl-2-butenyl acetate can be used for producing a cyclopropane compound, which is important as an intermediate of synthesized pyrethroid, by reacting it with a diazoacetic acid ester (e.g. non-patent document 1).

As methods for producing 3-methyl-2-butenyl acetate, for example, a method which comprises reacting 3-methyl-2-buten-1-ol with acetic anhydride in the presence of excess of an amine compound (e.g. non-patent document 2 and 3) and a method which comprises reacting 3-methyl-2-buten-1-ol with acetic anhydride in the presence of an acid catalyst such as magnesium perchlorate and indium chloride (e.g. non-patent document 4 and 5) have been known. However, the former method has a problem of the wastewater treatment because of use of excess amounts of the amine compound. The latter method has a problem of the low yield and many impurities, or the availability of the catalyst and handling thereof. Any methods were not industrially satisfied.

Non-patent document 1: Tetrahedron, 57, 6083-6088 (2001)

Non-patent document 2: J. Chem. Soc., Perkin Trans. 1, 710-712 (2002)

Non-patent document 3: J. Org. Chem., 55, 5312-5323 (1990)

Non-patent document 4: Tetrahedron, 59, 7661-7668 (2003)

Non-patent document 5: Tetrahedron Letters, 44, 6749-6753 (2003)

DISCLOSURE OF THE INVENTION

According to the present invention, 3-methyl-2-butenyl acetate which is useful as a raw material of various chemicals such as pharmaceuticals and agricultural chemicals can be produced inexpensively and efficiently. Therefore, it is industrially advantageously.

That is, the first embodiment of the present invention relates to a method for producing 3-methyl-2-butenyl acetate which comprises reacting 3-methyl-2-buten-1-ol with acetic anhydride in the presence of an inorganic base catalyst. Further, the second embodiment of the present invention relates to a method for producing purified 3-methyl-2-butenyl acetate which comprises subjecting crude 3-methyl-2-butenyl acetate to a step (A) of making it contact with an aqueous solution of an alkali metal hydrogen sulfite, or a step (B) of making it contact with an aqueous solution of a base, or both steps (A) and (B).

BEST MODE FOR CARRYING OUT THE PRESENT INVENTION

The present invention will be illustrated in detail below.

In the first embodiment of the present invention, examples of the inorganic base used as a catalyst include an alkali metal hydroxide such as potassium hydroxide, sodium hydroxide and lithium hydroxide; an alkaline earth metal hydroxide such as magnesium hydroxide and calcium hydroxide; an alkali metal carbonate such as potassium carbonate, sodium carbonate and lithium carbonate; an alkaline earth metal carbonate such as magnesium carbonate and calcium carbonate; an alkali metal hydrogen carbonate such as potassium hydrogen carbonate, sodium hydrogen carbonate and lithium hydrogen carbonate; an alkaline earth metal carbonate such as magnesium hydrogen carbonate and calcium hydrogen carbonate; an alkali metal acetate such as potassium acetate, sodium acetate and lithium acetate; an alkaline earth metal acetate such as magnesium acetate and calcium acetate; and an aluminum compound such as aluminum hydroxide, aluminum carbonate, aluminum hydrogen carbonate and aluminum acetate. Among them, preferred is the alkali metal acetate and more preferred is potassium acetate because of the good properties of the reaction liquid.

The amount of the base to be used is usually in the range of 0.001 to 0.5 mole, preferably in the range of about 0.01 to 0.2 mole relative to 1 mole of 3-methyl-2-buten-1-ol.

The amount of acetic anhydride to be used is usually 1 mole or more, preferably in the range of about 1 to 1.5 moles relative to 1 mole of 3-methyl-2-buten-1-ol.

An inert solvent may be used in the reaction, if necessary. Examples of the inert solvent include aromatic hydrocarbon solvents such as toluene, xylene, mesitylene and chlorobenzene; aliphatic hydrocarbon solvents such as hexane, heptane, octane and cyclohexane; halogenated aliphatic hydrocarbon solvents such as dichloromethane, dichloroethane and carbon tetrachloride; ether solvents such as diethyl ether and tert-butyl methyl ether; aprotic polar solvents such as acetonitrile. When these solvents are used, the amount thereof is not particularly limited and it is usually 100 parts by weight or less relative to 1 part by weight of 3-methyl-2-buten-1-ol.

The reaction temperature of the present reaction is usually 0° C. or more and below the boiling point of the reaction system. The reaction temperature is preferably in the range of about 20 to 80° C.

The present reaction may be carried out under an atmospheric pressure condition and under a pressurized condition. The congress of the reaction can be confirmed by a conventional analytical means such as gas chromatography, high-performance liquid chromatography, thin layer chromatography, NMR and IR. The reaction is preferably carried out under an atmosphere of an inert gas such as an atmosphere of nitrogen gas.

The mixing order of 3-methyl-2-buten-1-ol, acetic anhydride and the base catalyst is not particularly limited and, for example, the reaction can be also carried out by adding acetic anhydride into the mixture of 3-methyl-2-buten-1-ol and the base catalyst.

After the reaction, most of acetic acid produced as by-product in the reaction can be removed by adding water to the reaction mixture, washing, and if necessary, extracting with a water-immiscible organic solvent and conducting a separation operation. At the same time, acetic anhydride remained is hydrolyzed to acetic acid and removed. The operation temperature of washing with water is usually 0 to 80° C., preferably in the range of about 10 to 50° C. Thus, 3-methyl-2-butenyl acetate is obtained as an organic layer. It may be used as it is and if necessary, it may be further purified by a conventional purification means such as distillation treatment.

When by-products, which are difficult to remove by distillation treatment such as a carboxylic acid such as acetic acid and/or an aldehyde such as 3-methyl-2-butenal, are contained as impurities in the organic layer obtained, impurities can be removed from the product, crude 3-methyl-2-butenyl acetate, by the above-mentioned step (A), step (B) or both steps (A) and (B) to obtain purified 3-methyl-2-butenyl acetate.

Crude 3-methyl-2-butenyl acetate is subjected to the above-mentioned step (A) and/or (B) as it is or as a solution of a water-immiscible organic solvent. Examples of the water-immiscible organic solvent include aromatic hydrocarbon solvents such as toluene, xylene, mesitylene and chlorobenzene; aliphatic hydrocarbon solvents such as hexane, heptane, octane and cyclohexane; ester solvents such as ethyl acetate and diethyl carbonate; halogenated aliphatic hydrocarbon solvents such as dichloromethane, dichloroethane and carbon tetrachloride; and ether solvents such as diethyl ether and tert-butyl methyl ether.

In the step (A), making crude 3-methyl-2-butenyl acetate contact with an aqueous solution of an alkali metal hydrogen sulfite is usually carried out by stirring and mixing both and the mixing order is not particularly limited and the two layers are preferably stirred enough to mix them thoroughly.

Examples of the alkali metal hydrogen sulfite include sodium hydrogen sulfite and potassium hydrogen sulfite. The amount of the alkali metal hydrogen sulfite to be used may be usually 1 mole or more relative to 1 mole of the aldehyde contained therein, and there is no specific upper limit.

The concentration of the aqueous solution of the alkali metal hydrogen sulfite is usually in the range of 0.5 to 50% by weight, preferably in the range of about 1 to 40% by weight. The treatment temperature is usually in the range of 0 to 100° C., preferably in the range of about 30 to 60° C.

After making crude 3-methyl-2-butenyl acetate contact with the aqueous solution of the alkali metal hydrogen sulfite, 3-methyl-2-butenyl acetate can be obtained as an organic layer by separating an organic layer and a water layer. The amount of the aldehyde contained in the 3-methyl-2-butenyl acetate mass obtained such as 3-methyl-2-butenal is usually about 0.1% by weight or less. In order to conduct to remove the aldehyde further enough, the organic layer obtained is preferably treated with water and separated the organic layer and the water layer to obtain the organic layer. In this case, the amount of water to be used, the treatment temperature and treatment time may be carried out according to the above-mentioned treatment with the aqueous solution of the alkali metal hydrogen sulfite.

In the step (B), making crude 3-methyl-2-butenyl acetate contact with the aqueous solution of the base is usually carried out by stirring and mixing both and the mixing order is not particularly limited and the two layers is preferably stirred enough to mix them thoroughly.

Examples of the base include an alkali metal hydroxide such as sodium hydroxide and potassium hydroxide; an alkali metal carbonate such as sodium carbonate and potassium carbonate; and an alkali metal hydrogen carbonate such as sodium hydrogen carbonate and potassium hydrogen carbonate. In the viewpoint of inhibiting the hydrolysis of 3-methyl-2-butenyl acetate, use of the alkali metal hydrogen carbonate is preferred. Similarly, the amount of the base to be used is also usually in the range of about 1 to 5 moles relative to 1 mole of the carboxylic acid and the purpose can be accomplished.

The concentration of the aqueous solution of the base is usually in the range of 0.5 to 50% by weight, preferably in the range of about 1 to 40% by weight. The treatment temperature is usually in the range of 0 to 50° C., preferably in the range of about 5 to 30° C. The treatment time is usually in the range of about 5 minutes to 2 hours.

After treating crude 3-methyl-2-butenyl acetate with the aqueous solution of the base, 3-methyl-2-butenyl acetate can be obtained as an organic layer by separating an organic layer and a water layer. The amount of the carboxylic acid contained in the 3-methyl-2-butenyl acetate mass obtained is usually about 0.1% by weight or less. In order to conduct to remove the carboxylic acid further enough and inhibit the congress of hydrolysis of 3-methyl-2-butenyl acetate by the remained base, the organic layer obtained is preferably treated with water and separated an organic layer and a water layer to obtain the organic layer. The amount of water to be used, the treatment temperature and treatment time in this case may be carried out according to the above-mentioned treatment with the aqueous solution of the base.

Depending on kinds of impurities to be removed, only either step of the above-mentioned step (A) and (B) can be subjected and naturally, both steps may be subjected. That is, in order to remove the aldehyde, the step (A) may be subjected and in order to remove the carboxylic acid, the step (B) may be subjected. When both steps are subjected, the order of steps is not particularly limited, and the step (B) may be subjected after the step (A) is subjected and in inverted order. However, there is a possibility of remaining of an acidic material such as sulfurous acid gas derived from the alkali metal hydrogen sulfite in the step (A), and in order to remove the acidic material, the step (B) is preferably subjected after the step (A) is subjected. When the step (A) is only subjected, in order to remove the above-mentioned acidic material of which there is a possibility of remaining such as sulfurous acid gas, an inert gas may be blown into 3-methyl-2-butenyl acetate obtained. The step (A) and (B) are preferably carried out under an inert atmosphere such as nitrogen gas.

Purified 3-methyl-2-butenyl acetate thus obtained may be further purified, if necessary, by a conventional purification method such as distillation treatment.

EXAMPLES

The present invention will be further illustrated in more detail by Examples below. The present invention is not limited to Examples. In Examples, either of contents of 3-methyl-2-butenyl acetate and impurities containing in it were calculated by a percentage of a peak area in gas chromatogram.

Example 1

Reaction Step

Under an atmosphere of nitrogen, 140.6 g (1.60 mol) of 3-methyl-2-buten-1-ol (content: 98% by weight) and 16.2 g (0.16 mol) of potassium acetate (content: 97% by weight) were mixed and the mixture was heated to 48 to 52° C. 176.8 g (1.68 mol) of acetic anhydride (content: 97% by weight) was added dropwise thereto over 5 hours and then the mixture was continuously stirred at the same temperature for 6 hours. The reaction mixture was analyzed by gas chromatography internal standard method to find the yield of 3-methyl-2-butenyl acetate was 100% (based on 3-methyl-2-buten-1-ol). The reaction mixture was cooled to 28 to 32° C. After 35.2 g of water was added dropwise thereto over 1 hour, 105.5 g of water was added thereto and the mixture was continuously stirred at the same temperature for 1 hour. The reaction mixture was stood and separated to obtain 261.5 g of the organic layer containing 3-methyl-2-butenyl acetate.

<GC area percentage>3-methyl-2-butenyl acetate: 92.67%
  3-methyl-2-butenal: 0.06%
  acetic acid: 6.49%

Example 2

Purification Step 83.7 g of 5% aqueous sodium hydrogen sulfite was added to the organic layer obtained in Example 1 and the mixture was stirred at 20 to 30° C. for 1 hour and then the mixture was stood and separated to obtain the organic layer. 70.3 g of water was added to the organic layer and the mixture was stirred at the same temperature for 30 minutes and then the mixture was stood and separated to obtain the organic layer. The organic layer was cooled to 15 to 25° C. and 44.9 g of 30% aqueous potassium carbonate was added dropwise thereto and then 67.3 g of 5% aqueous sodium hydrogen carbonate was added thereto. The mixture was stirred at the same temperature for 30 minutes and then the mixture was stood and separated to obtain the organic layer. 70.3 g of water was added to the organic layer and the mixture was stirred at the same temperature for 30 minutes and then the mixture was stood and separated. The organic layer obtained was analyzed by gas chromatography internal standard method to find the yield of 3-methyl-2-butenyl acetate was 94.6% (based on 3-methyl-2-buten-1-ol). The simple distillation of this organic layer was carried out under an atmosphere of nitrogen to obtain 193.3 g of the colorless oil of 3-methyl-2-butenyl acetate. The yield after distillation purification was 93.5% (based on 3-methyl-2-buten-1-ol). The boiling point was 70 to 71° C./5 kPa and moisture was 53 ppm.

<GC area percentage>3-methyl-2-butenyl acetate: 99.24%
3-methyl-2-butenal: 0.01%
acetic acid: Not detected

Example 3

Reaction Step

Under an atmosphere of nitrogen, 552.9 g (6.40 mol) of 3-methyl-2-buten-1-ol (content: 99.7% by weight) and 48.6 g (0.48 mol) of potassium acetate (content: 97% by weight) were mixed and the mixture was heated to 48 to 52° C. 707.3 g (6.72 mol) of acetic anhydride (content: 97% by weight) was added dropwise thereto over 5.5 hours and then the mixture was continuously stirred at the same temperature for 9 hours. The reaction mixture was analyzed by gas chromatography internal standard method to find the yield of 3-methyl-2-butenyl acetate was 100% (based on 3-methyl-2-buten-1-ol). The reaction mixture was cooled to 28 to 32° C. After 138 g of water was added dropwise thereto over 1 hour, 415 g of water was added thereto and the mixture was continuously stirred at the same temperature for 1 hour. The reaction mixture was stood and separated to obtain 1045.7 g of the organic layer containing 3-methyl-2-butenyl acetate.

<GC area percentage> 3-methyl-2-butenyl acetate: 92.64%
3-methyl-2-butenal: 0.02%
acetic acid: 6.85%

Example 4

Purification Step 335 g of 5% aqueous sodium hydrogen sulfite was added to the organic layer obtained in Example 3 and the mixture was stirred at 20 to 30° C. for 1 hour and then the mixture was stood and separated to obtain the organic layer. 277 g of water was added to the organic layer and the mixture was stirred at the same temperature for 30 minutes and then the mixture was stood and separated to obtain the organic layer. The organic layer was cooled to 15 to 25° C. and 235 g of 30% aqueous potassium carbonate was added thereto at the same temperature. The mixture was stirred at the same temperature for 30 minutes and then the mixture was stood and separated to obtain the organic layer. 277 g of water was added to the organic layer and the mixture was stirred at the same temperature for 30 minutes and then the mixture was stood and separated. The organic layer obtained was analyzed by gas chromatography internal standard method to find the yield of 3-methyl-2-butenyl acetate was 94.2% (based on 3-methyl-2-buten-1-ol). The simple distillation of this organic layer obtained was carried out under an atmosphere of nitrogen to obtain 733.3 g of the colorless oil of 3-methyl-2-butenyl acetate. The yield after purification was 89.4% (based on 3-methyl-2-buten-1-ol). The boiling point was 70 to 71° C./5 kPa and moisture was 24 ppm.

<GC area percentage> 3-methyl-2-butenyl acetate: 99.73%
3-methyl-2-butenal: Not detected
acetic acid: Not detected

Example 5

135 g of 5% aqueous sodium hydrogen sulfite was added to crude 3-methyl-2-butenyl acetate containing 97.88% of 3-methyl-2-butenyl acetate, 0.34% of acetic acid and 0.62% of 3-methyl-2-butenal. The mixture was stirred at 40 to 50° C. for 30 minutes and then the mixture was stood and separated to obtain the organic layer. 135 g of water was added to the organic layer and the mixture was stirred at the same temperature for 10 minutes and then the mixture was stood and separated to obtain the organic layer. The organic layer was cooled to 15 to 25° C. and 135 g of 5% aqueous sodium hydrogen carbonate was added thereto and the mixture was stirred at the same temperature for 30 minutes and then the mixture was stood and separated to obtain the organic layer. 135 g of water was added to the organic layer and the mixture was stirred and washed at the same temperature for 10 minutes and then the mixture was stood and separated. The simple distillation of the organic layer obtained was carried out under an atmosphere of nitrogen to obtain 197 g of 3-methyl-2-butenyl acetate. Boiling point 70 to 71° C./5 kPa 99.31% of 3-methyl-2-butenyl acetate and 0.01% of 3-methyl-2-butenal were contained in purified 3-methyl-2-butenyl acetate and acetic acid was not detected.

Reference Example 1

Into a 50 mL Schlenk tube purged with nitrogen, 5.2 mg of copper(I) trifluoromethanesulfonate-toluene complex, 6.7 mg of 1,1-bis[(4S)-tert-butyl-2-oxazoline]cyclopropane and 7.5 mL of purified 3-methyl-2-butenyl acetate obtained in Example 5 were added and the mixture was stirred at 21° C. for 30 minutes to prepare the asymmetric copper catalyst. After that, the solution obtained by dissolving 2.3 g of ethyl diazoacetate to 3.8 mL of purified 3-methyl-2-butenyl acetate obtained in Example 1 was added dropwise thereto at the same temperature over 4 hours and the mixture was stirred at the same temperature for 30 minutes to effect reaction. The solution containing ethyl 2,2-dimethyl-3-(acetoxymethyl)cyclopropanecarboxylate was obtained. The yield thereof was 72% (based on ethyl diazoacetate).

Reference Example 2

According to the same manner as that described in Reference Example 1, the yield of ethyl 2,2-dimethyl-3-(acetoxymethyl)cyclopropanecarboxylate was 57% (based on ethyl diazoacetate) except that crude 3-methyl-2-butenyl acetate used in Example 1 was used in place of purified 3-methyl-2-butenyl acetate obtained in Example 5.

INDUSTRIAL APPLICABILITY

According to the present invention, 3-methyl-2-butenyl acetate which is useful as a raw material of various chemicals such as pharmaceuticals and agricultural chemicals can be produced inexpensively and efficiently and therefore, it is industrially advantageous.

The invention claimed is:

1. A method for producing purified 3-methyl-2-butenyl acetate which comprises subjecting crude 3-methyl-2-butenyl acetate to a step (A) of making it contact with an aqueous solution of an alkali metal hydrogen sulfite, or both step (A) and a step (B) of making it contact with an aqueous solution of a base.

2. The method according to claim 1, which comprises subjecting crude 3-methyl-2-butenyl acetate to the step (A), and next to the step (B).

3. The method according to claim 2, wherein the aqueous solution of the base is an aqueous solution of an alkali metal hydrogen carbonate.

4. The method according to claim 1, wherein an impurity contained in the crude 3-methyl-2-butenyl acetate is carboxylic acid and/or an aldehyde.

5. The method according to claim 1, wherein the crude 3-methyl-2-butenyl acetate is obtained by reacting 3-methyl-2-buten-1-ol with acetic anhydride in the presence of an inorganic base catalyst.

* * * * *